US009739793B2

(12) United States Patent
Furusato et al.

(10) Patent No.: US 9,739,793 B2
(45) Date of Patent: Aug. 22, 2017

(54) ANALYSIS METHOD, ANALYSIS DEVICE, PROGRAM USED TO IMPLEMENT SAID ANALYSIS METHOD, AND STORAGE MEDIUM AND RETRIEVAL DEVICE FOR THIS PROGRAM (75) Inventors: Noriaki Furusato, Kyoto (JP); Kousuke Kubo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 451 days.

(21) Appl. No.: 13/201,046

(22) PCT Filed: Jan. 31, 2010

(86) PCT No.: PCT/JP2010/051298
§ 371 (c)(1),
(2), (4) Date: Aug. 11, 2011

(87) PCT Pub. No.: WO2010/092883
PCT Pub. Date: Aug. 19, 2010

(65) Prior Publication Data
US 2011/0300565 A1 Dec. 8, 2011

(30) Foreign Application Priority Data

Feb. 12, 2009 (JP) ................. 2009-029511

(51) Int. Cl.
*C12Q 1/54* (2006.01)
*G01N 1/10* (2006.01)
(Continued)

(52) U.S. Cl.
CPC ... *G01N 35/026* (2013.01); *G01N 2035/0094* (2013.01)

(58) Field of Classification Search
CPC combination set(s) only.
See application file for complete search history.

(56) References Cited

U.S. PATENT DOCUMENTS 3,917,455 A 11/1975 Bak et al.
5,876,670 A 3/1999 Mitsumaki et al.
(Continued)

FOREIGN PATENT DOCUMENTS

EP 0628823 A 6/1994
EP 0 745 855 A2 12/1996
(Continued)

OTHER PUBLICATIONS

The Examination Report issued by the Indian Patent Office dated Feb. 20, 2017, which corresponds to Indian Patent Application No. 6043/CHENP/2011 and is related to U.S. Appl. No. 13/201,046.

*Primary Examiner* — Jill Warden
*Assistant Examiner* — Julie Tavares
(74) *Attorney, Agent, or Firm* — Studebaker & Brackett PC (57) ABSTRACT An analysis apparatus includes a first analysis unit which collects samples by utilizing a first nozzle to analyze the sample, a second analysis unit which collects samples by utilizing a second nozzle to analyze the sample, and a transport apparatus which transports a plurality of sample vessels along a predetermined transport route. When a predetermined waiting state is provided such that the transport of the plurality of sample vessels is interrupted or stopped, then the sample collecting position is changed for at least one of the first and second nozzles, and the samples are collected from the plurality of sample vessels by means of the nozzle having the changed position. Accordingly, it is possible to enhance the efficiency of the analysis process performed by the analysis apparatus, while suppressing the transport apparatus from being large-sized and suppressing the structure from being complicated.

14 Claims, 9 Drawing Sheets (51) Int. Cl.
*C12M 1/26* (2006.01)
*G06F 17/00* (2006.01)
*C12M 1/34* (2006.01)
*C12Q 1/02* (2006.01)
*G01N 35/02* (2006.01)
*G01N 35/00* (2006.01)

(56) References Cited

U.S. PATENT DOCUMENTS

| | | | |
|---|---|---|---|
| 5,985,215 | A | 11/1999 | Sakazume et al. |
| 6,319,718 | B1 | 11/2001 | Matsubara et al. |
| 6,588,625 | B2 | 7/2003 | Luoma, II et al. |
| 6,723,288 | B2 * | 4/2004 | Devlin et al. ............ 422/65 |
| 6,805,840 | B1 | 10/2004 | Tajima |
| 6,924,152 | B2 | 8/2005 | Matsubara et al. |
| 7,105,351 | B2 | 9/2006 | Matsubara et al. |
| 7,458,483 | B2 | 12/2008 | Luoma, II |
| 7,597,848 | B1 | 10/2009 | Ameling et al. |
| 2003/0202905 | A1* | 10/2003 | Devlin, Sr. ........ G01N 35/04 422/64 |
| 2005/0118066 | A1 | 6/2005 | Ikeda et al. |
| 2005/0150314 | A1 | 7/2005 | Staples et al. |
| 2005/0186113 | A1* | 8/2005 | Koike et al. ............ 422/63 |
| 2008/0067079 | A1 | 3/2008 | Takahashi et al. |

FOREIGN PATENT DOCUMENTS

| | | |
|---|---|---|
| EP | 2 023 150 A2 | 2/2009 |
| JP | 01-015029 B | 1/1983 |
| JP | 01-046030 B | 3/1994 |
| JP | 3403229 B | 8/1994 |
| JP | 07-092171 A | 4/1995 |
| JP | 3031242 B | 11/1997 |
| JP | H10-096734 A | 4/1998 |
| JP | 10-227800 A | 8/1998 |
| JP | 11-304814 A | 11/1999 |
| JP | 11-304818 A | 11/1999 |
| JP | 3031374 B | 11/1999 |
| JP | 3609945 B | 3/2000 |
| JP | 3616744 B | 12/2001 |
| JP | 2002-522768 A | 7/2002 |
| JP | 2003-149255 A | 5/2003 |
| JP | 2004-525376 A | 8/2004 |
| JP | 2006-349460 A | 12/2006 |
| JP | 2008-070210 A | 3/2008 |
| RU | 2365920 C2 | 8/2009 |
| SU | 677682 A3 | 7/1979 |

* cited by examiner

ANALYSIS METHOD, ANALYSIS DEVICE, PROGRAM USED TO IMPLEMENT SAID ANALYSIS METHOD, AND STORAGE MEDIUM AND RETRIEVAL DEVICE FOR THIS PROGRAM

INCORPORATION BY REFERENCE

The present application is a 371 of International Application No. PCT/JP2010/051298, filed Jan. 31, 2010, which claims priority to Japanese Patent Application No. 2009-029511, filed Feb. 12, 2009, the entire contents of which being hereby incorporated herein by reference.

TECHNICAL FIELD

The present invention relates to an analysis method, an analysis apparatus, a program used to carry out the analysis method, a storage medium for the program, and a collecting apparatus (sampling apparatus) in order to analyze a desired sample including, for example, blood and urine.

BACKGROUND ART

Conventionally, a specified example of an analysis apparatus for analyzing a sample such as blood, urine or the like is known, wherein first and second analysis units, which deal with different analysis process contents, are combined with a transport apparatus which successively supplies a plurality of sample vessels to the first and second analysis units (see, for example, Patent documents 1 to 4). For example, a unit, in which samples are collected by utilizing a suction nozzle from a plurality of sample vessels transported by the transport apparatus and the collected samples are reacted with a predetermined reagent to perform the analysis, is used as each of the first and second analysis units. According to the arrangement as described above, the plurality of sample vessels can be successively transported to the first and second analysis units by utilizing the transport apparatus, and the analysis processes may be efficiently performed for the samples accommodated in the respective sample vessels.

However, the conventional technique described above involves drawbacks to be improved as described below.

That is, in order to deliver the sample vessel from the first analysis unit to the second analysis unit, it is necessary that the second analysis unit should be in such a condition that the sample vessel may be accepted. Therefore, it is necessary to provide a waiting state in which the driving of the transport apparatus is stopped, when the analysis process is not completed in the second analysis unit and the second analysis unit is not in such a condition that the sample vessel can be accepted, even when the analysis process is completed in the first analysis unit. The waiting state as described above tends to arise frequently when the analysis process speed of the second analysis unit is slower than that of the first analysis unit. Further, the waiting state as described above also arises when the second analysis unit stops the analysis process on the basis of such a reason that the suction nozzle is washed for a long period of time.

On the other hand, the sample collecting positions (positions at which the samples are collected from the sample vessels) are always constant for the respective suction nozzles provided for the first and second analysis units. Therefore, in the conventional technique described above, when the waiting state, in which the driving of the transport apparatus is stopped, is brought about resulting from the delay or the stop of the analysis process performed by the second analysis unit, it is also difficult for the first analysis unit to execute the collection of the next new sample and the analysis process therefor. In such a situation, a malfunction or inconvenience arises such that the efficiency of the analysis process is lowered. In view of the enhancement of the analysis process efficiency, it is demanded that the period of time, in which both of the first and second analysis units are stopped, should be suppressed from being continuously prolonged as far as possible.

The following means is conceived as one means for suppressing the inconvenience as described above. That is, a plurality of transport apparatuses are used as the transport means for transporting the sample vessels, and a stock area is provided between the first and second analysis units in order to store the large number of sample vessels. According to the means as described above, even when the supply of the sample vessel to the second analysis unit is stopped, then the sample vessel can be discharged from the first analysis unit to the stock area, while the sample vessel can be newly supplied to the first analysis unit to execute the analysis process for the sample. However, if the means as described above is adopted, it is necessary that the stock area should be provided to have a relative large areal size between the first and second analysis units. Therefore, the transport apparatus is consequently large-sized, and the entire analysis apparatus is consequently large-sized. Additionally, the structure of the transport apparatus is complicated, and the production cost thereof is expensive as well.

PRECEDING TECHNICAL DOCUMENT

Patent Document

[Patent document 1] Japanese Patent No. 3616744
[Patent document 2] Japanese Patent Application Laid-open No. 7-92171
[Patent document 3] Japanese Patent No. 3031242
[Patent document 4] Japanese Patent No. 3031374

DISCLOSURE OF THE INVENTION

Problems to be Solved by the Invention

An object of the present invention is to provide an analysis method, an analysis apparatus, a program used to carry out the analysis method, a storage medium for the program, and a collecting apparatus (sampling apparatus) which make it possible to appropriately suppress or dissolve the malfunction or inconvenience as described above.

Means for Solving the Problems

In order to solve the problem as described above, the present invention adopts the following technical means.

According to a first aspect of the present invention, there is provided an analysis method comprising a step of transporting a plurality of sample vessels along a predetermined transport route; a step of collecting samples from the plurality of sample vessels transported along the transport route by utilizing a first nozzle to execute an analysis process for the collected sample in a first analysis unit; and a step of collecting samples from the plurality of sample vessels by utilizing a second nozzle on a downstream side in the transport route from the first nozzle to execute an analysis process for the collected sample by a second analysis unit; the analysis method further comprising a step of changing a sample collecting position of at least one of the first and second nozzles to collect samples from the plurality of sample vessels by using the nozzle having the changed position when a predetermined waiting state is provided such that the transport of the plurality of sample vessels is interrupted or stopped.

According to a second aspect of the present invention, there is provided an analysis apparatus comprising a transport apparatus which transports a plurality of sample vessels along a predetermined transport route; a first analysis unit which collects samples from the plurality of transported sample vessels by utilizing a first nozzle and which is capable of executing a predetermined analysis process for the collected sample; and a second analysis unit which collects samples from the plurality of sample vessels by utilizing a second nozzle on a downstream side in the transport route from the first nozzle and which is capable of executing a predetermined analysis process for the collected sample; wherein a sample collecting position is changed for at least one of the first and second nozzles and samples are collected from the plurality of sample vessels by means of the nozzle having the changed position when a predetermined waiting state is provided such that the transport of the plurality of sample vessels is interrupted or stopped.

Preferably, the sample collecting positions are changeable for both of the first and second nozzles; and the sample collecting position of the second nozzle is changed to collect the samples from the plurality of sample vessels so that the analysis process for the sample is executed by the second analysis unit when the predetermined waiting state is provided on the basis of the interruption or the stop of the analysis process in the first analysis unit; while the sample collecting position of the first nozzle is changed to collect the samples from the plurality of sample vessels so that the analysis process for the sample is executed by the first analysis unit when the predetermined waiting state is provided on the basis of the interruption or the stop of the analysis process in the second analysis unit.

Preferably, the first nozzle has the sample collecting position which is changeable in a sample vessel transport direction and a direction opposite thereto, and the sample collecting position of the first nozzle is changed in the direction opposite to the sample vessel transport direction when the predetermined waiting state is provided.

Preferably, the second nozzle has the sample collecting position which is changeable in a sample vessel transport direction and a direction opposite thereto, and the sample collecting position of the second nozzle is changed in the direction opposite to the sample vessel transport direction when the predetermined waiting state is provided.

Preferably, the second nozzle has the sample collecting position which is changed until arrival at an upstream area in a sample vessel transport direction as compared with the sample collecting position of the first nozzle, and the second nozzle is capable of collecting the sample which is not collected by the first nozzle.

Preferably, the first and second nozzles have the sample collecting positions which are changeable in a direction intersecting the sample vessel transport direction, and the first and second nozzles are capable of collecting the samples from the plurality of sample vessels respectively even when the plurality of sample vessels are transported in a plurality of arrays by means of the transport apparatus.

Preferably, the first and second analysis units are accommodated and integrated in one casing.

Preferably, the first and second analysis units are capable of analyzing blood or urine.

Preferably, the first analysis unit is capable of measuring a blood glucose level, and the second analysis unit is capable of measuring glycohemoglobin.

Preferably, the first analysis unit is an apparatus for urine qualitative analysis, and the second analysis unit is an apparatus for urine sediment analysis.

Preferably, the plurality of sample vessels are a plurality of blood collecting vessels (tubes) or urine collecting vessels (tubes) which are held in a rack so that the vessels (tubes) are aligned in one array or a plurality of arrays.

Preferably, at least one of the first and second analysis units is constructed to analyze only a part of the selected sample or samples of the plurality of supplied samples; and a number of the sample or samples subjected to the analysis differs between the first and second analysis units.

Preferably, a period of time, which is required to analyze one sample, differs between the first and second analysis units.

Preferably, the first analysis unit deals with a large number of the samples subjected to the analysis as compared with the second analysis unit, and the first analysis unit requires a short period of time required to analyze one sample as compared with the second analysis unit.

According to a third aspect of the present invention, there is provided a program to be used for driving an analysis apparatus comprising a first analysis unit which collects samples from a plurality of sample vessels transported by a transport apparatus by utilizing a first nozzle and which is capable of executing a predetermined analysis process for the collected sample; a second analysis unit which collects samples from the plurality of sample vessels by utilizing a second nozzle on a downstream side in a transport route from the first nozzle and which is capable of executing a predetermined analysis process for the collected sample; and control means which controls operations of the first and second analysis units; wherein the program includes data for executing a step of changing a sample collecting position of at least one of the first and second nozzles to collect samples from the plurality of sample vessels by using the nozzle having the changed position when a predetermined waiting state is provided such that the transport of the plurality of sample vessels is interrupted or stopped, in accordance with the control of the control means.

Preferably, the program according to the present invention includes data for executing, in accordance with the control of the control means, a step of changing the sample collecting position of the second nozzle to collect the samples from the plurality of sample vessels so that the analysis process for the sample is executed by the second analysis unit when the predetermined waiting state is provided on the basis of the interruption or the stop of the analysis process in the first analysis unit; and a step of changing the sample collecting position of the first nozzle to collect the samples from the plurality of sample vessels so that the analysis process for the sample is executed by the first analysis unit when the predetermined waiting state is provided on the basis of the interruption or the stop of the analysis process in the second analysis unit.

According to a fourth aspect of the present invention, there is provided a storage medium which stores the program provided according to the third aspect of the present invention.

According to a fifth aspect of the present invention, there is provided a collecting apparatus (sampling apparatus) comprising a transport unit which transports a plurality of sample vessels along a predetermined transport route; a first nozzle which collects samples from the plurality of sample vessels transported by the transport unit to supply the sample to a predetermined portion; and a second nozzle which collects samples from the plurality of sample vessels on a downstream side in the transport route from the first nozzle to supply the sample to a predetermined portion; wherein a sample collecting position is changed for at least one of the first and second nozzles and samples are collected from the plurality of sample vessels by means of the nozzle having the changed position when the transport unit is in a predetermined waiting state in which the transport of the plurality of sample vessels is stopped or interrupted.

The other features and advantages of the present invention will be further clarified from the following description of embodiments of the invention as explained with reference to the accompanying drawings.

MODE FOR CARRYING OUT THE INVENTION

A preferred embodiment of the present invention will be specifically explained below with reference to the drawings.

Figure 1:
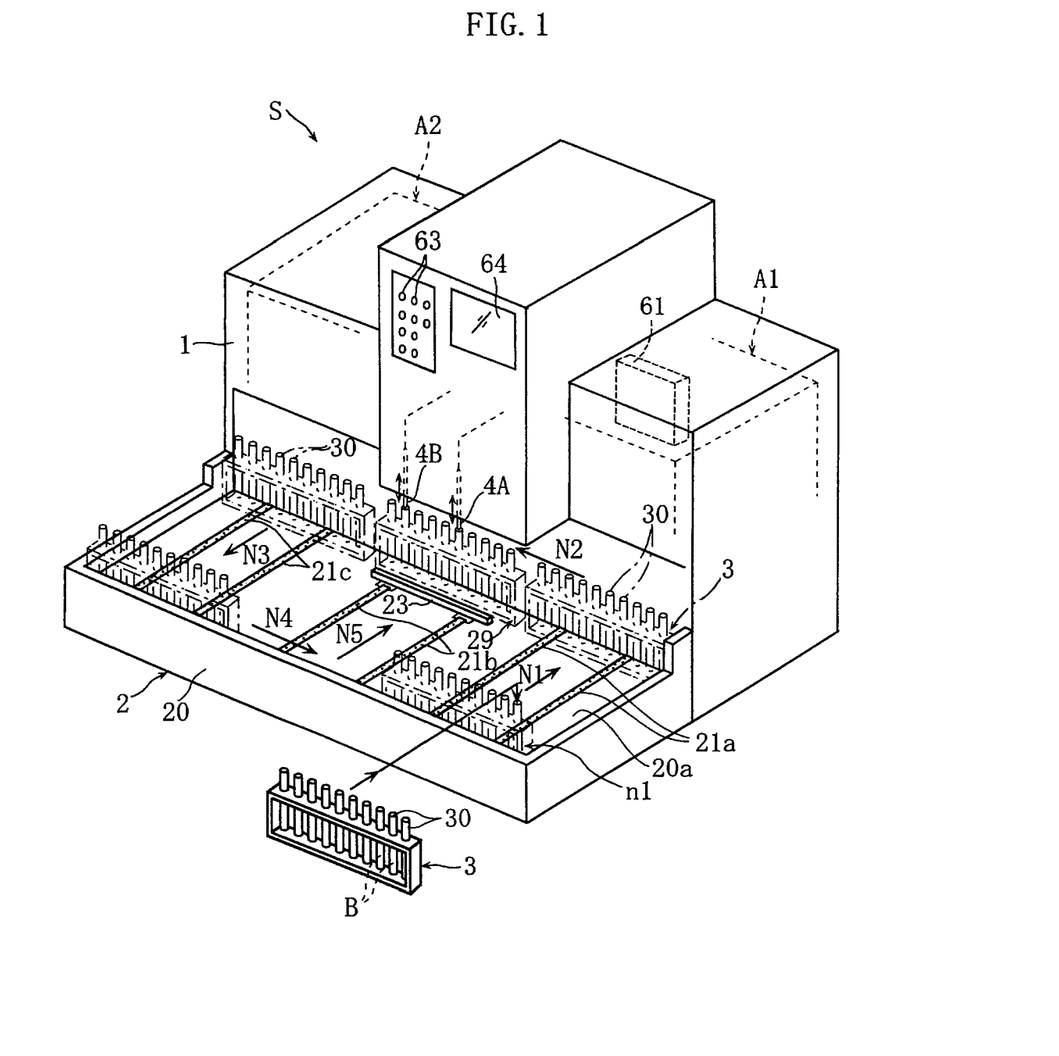
FIG. 1 shows a perspective view of the appearance illustrating an exemplary analysis apparatus according to the present invention.
Figure 2:
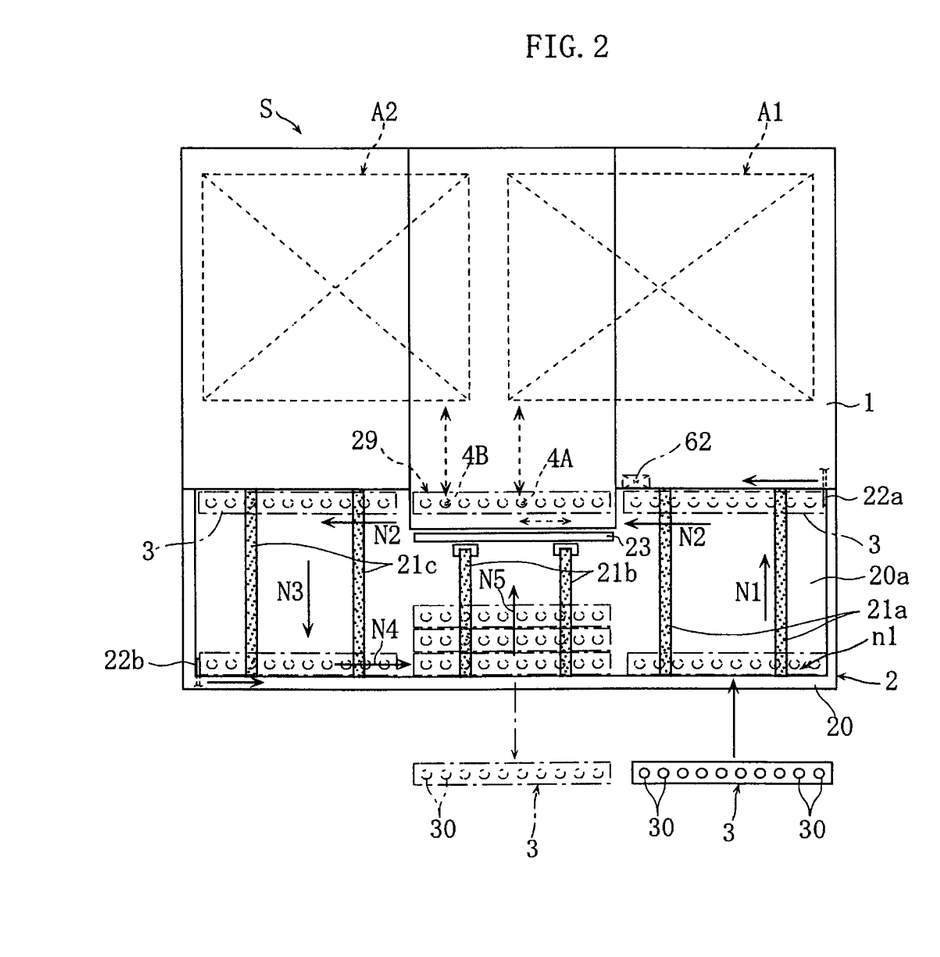
FIG. 2 shows a plan view illustrating those shown in FIG. 1.
Figure 3:
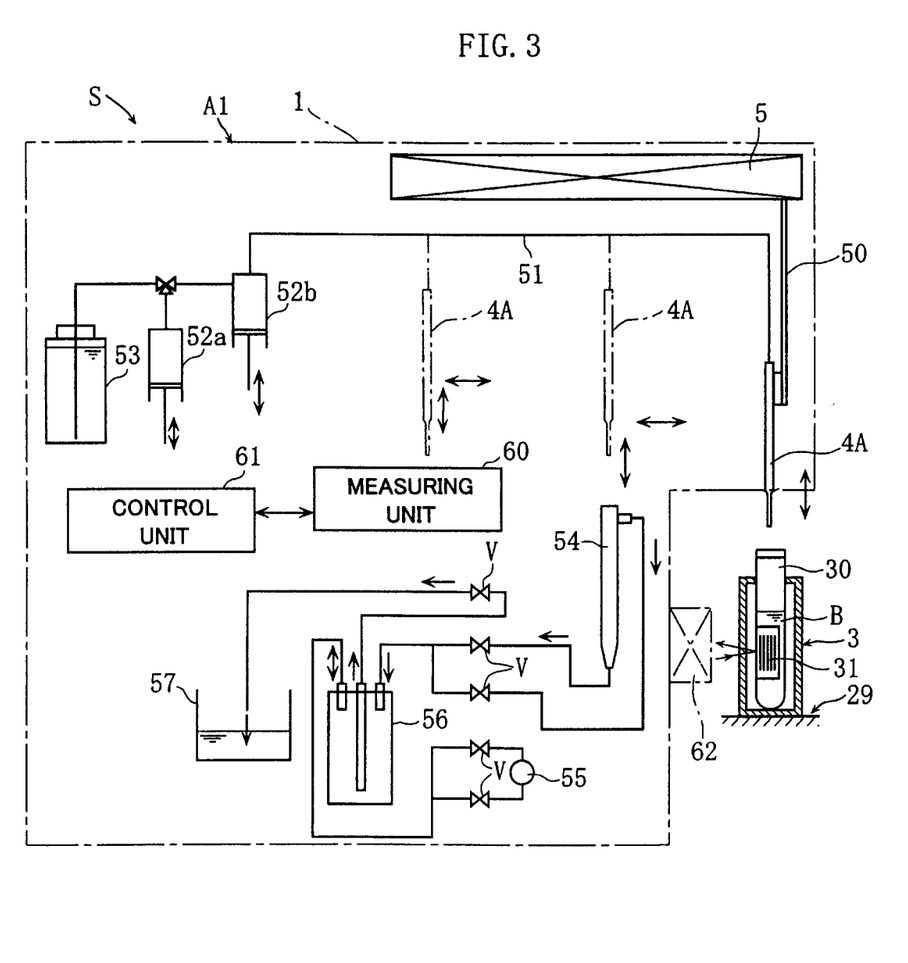
FIG. 3 shows a schematic arrangement of an analysis unit for constructing the analysis apparatus shown in FIGS. 1 and 2.

FIGS. 1 to 3 show an embodiment of an analysis apparatus to which the present invention is applied. As depicted in FIGS. 1 and 2, the analysis apparatus S of this embodiment comprises first and second analysis units A1, A2 which are accommodated and integrated in one casing 1, and a transport apparatus 2 which is provided to transport a plurality of blood collecting tubes (vessels) 30. The blood collecting tube 30 corresponds to an example of the sample vessel referred to in the present invention. Blood B, which is accommodated in the blood collecting tube 30, corresponds to an example of the sample referred to in the present invention.

The analysis apparatus S is provided in order that the blood B is analyzed to judge whether or not the diabetes arises. The first and second analysis units A1, A2 have first and second nozzles 4A, 4B which are capable of sucking and collecting the blood B from the blood collecting tube 30. The first analysis unit A1 measures the glucose concentration (blood glucose level) in the blood B collected by utilizing the first nozzle 4A. The second analysis unit A2 measures the concentration of glycohemoglobin such as hemoglobin A1c or the like in the blood B collected by utilizing the second nozzle 4B. However, in principle, the first analysis unit A1 deals with all blood samples B as analysis objectives supplied onto the transport apparatus 2, while the second analysis unit A2 deals with only blood samples B as analysis objectives for which any abnormal value concerning a predetermined range is detected in the analysis process performed by the first analysis unit A1. Therefore, the number of times of the analysis processes performed by the second analysis unit A2 is smaller than that of the first analysis unit A1. The period of time required for the analysis of 1 sample (period of time ranging from the start of the collection of the blood B by utilizing any one of the first and second nozzles 4A, 4B to arrive at the condition under which the collection of the next new blood B can be started after the completion of the analysis of the blood B) is, for example, 18 seconds in the first analysis unit A1, while the period of time required for the analysis of 1 sample is, for example, 36 seconds in the second analysis unit A2. Therefore, the analysis process speed of the first analysis unit A1 is higher than that of the second analysis unit A2.

As shown in FIG. 3, the first nozzle 4A is supported by an arm 50 of a nozzle moving apparatus 5, and the first nozzle 4A is movable in the upward-downward direction and the horizontal direction. However, as described later on, the first nozzle 4A has the sample collecting position over the transport apparatus 2, and the sample collecting position is changeable in the sample vessel transport direction N2 and the direction opposite thereto. The nozzle moving apparatus 5 is constructed by using driving means including, for example, a reciprocative cylinder and a circulating driving belt (any one of them is not shown).

The basic arrangement of the first analysis unit A1 is the same as or equivalent to the arrangement of any conventionally known glucose concentration measuring apparatus. That is, the first analysis unit A1 is provided with syringe pumps 52a, 52b connected via a tube 51 to an upper portion of the first nozzle 4A, a washing liquid tank 53, a washing vessel 54, a measuring unit 60, and a control unit 61. The syringe pumps 52a, 52b perform the operation in which the washing liquid stored in the washing liquid tank 53 is fed into the first nozzle 4A via the tube 51, and the operation in which the negative pressure for sucking the sample is generated in the first nozzle 4A. The washing vessel 54 is provided to wash the first nozzle 4A. The washing liquid is fed into the first nozzle 4A via the tube 51 in a state in which the first nozzle 4A is advanced into the washing vessel 54, and thus the first nozzle 4A is washed. The washing liquid, which is supplied into the washing vessel 54, is supplied to a waste liquid tank 57 via an intermediate bottle 56 in accordance with the switching operation of an air pump 55 and a plurality of opening/closing valves V.

The measuring unit 60 is provided with a dripping portion (not shown) which receives the dripping of the blood B from the first nozzle 4A, and an instrument (not shown) which is provided to measure the glucose concentration of the blood B dripped onto the dripping portion. A so-called glucose sensor method can be used as the technique for measuring the glucose concentration. The glucose sensor method is described, for example, in Japanese Patent Application Laid-open No. 10-293132. In this method, an enzyme electrode, which uses glucose oxidase (GOD), is utilized. The control unit 61 is constructed by using a microcomputer, which executes the process for calculating the glucose concentration from the measurement data obtained by the measuring unit 60, and the operation control for the respective portions of the first analysis unit A1. However, the control unit 61 also controls the operation of the second analysis unit A2 and the transport apparatus 2 as described later on.

An identification code 31 such as a bar code or the like is affixed to the blood collecting tube 30. The analysis apparatus S is provided with a reading unit 62 for reading the identification code 31. The identification data, which is read by the reading unit 62, is transmitted to the control unit 61, and the identification data is used as the reference data which is allowed to correlate with the data of the analysis process result of the blood B in the first and second analysis units A1, A2.

The basic arrangement of the second analysis unit A2 may be the same as or equivalent to the arrangement of any conventionally known glycohemoglobin concentration measuring apparatus. A latex immunoaggregation method can be used as the technique for measuring the glycohemoglobin concentration as described in Japanese Patent Application Laid-open No. 2001-83165. As for the second analysis unit A2, the analysis process item is different from that of the first analysis unit A1. However, the respective parts or components can be basically constructed in the same manner as those of the first analysis unit A1 shown in FIG. 3, any explanation of which is omitted.

As shown in FIG. 1, the casing 1 is provided with a plurality of operation switches 63 and a display 64 for displaying the data. The control unit 61 executes the operation control of the respective components of the analysis unit S in accordance with the program stored in the control unit 61 and the operation of the plurality of operation switches 63. Therefore, it is unnecessary for the second analysis unit A2 to provide any control unit exclusively provided therefor. However, unlike this arrangement, a control unit, which is exclusively provided for the second analysis unit A2, may be provided for the second analysis unit A2, and the operation instruction is given to this control unit from the control unit 61. Accordingly, it is possible to provide such an arrangement that the operation, which corresponds to the instruction, is executed in the second analysis unit A2.

The rack 3, which holds the plurality of blood collecting tubes 30 in an upstanding attitude, is transported along a constant route by the transport apparatus 2. The plurality of blood collecting tubes 30 are aligned in one array at constant pitches on the rack 3. The transport apparatus 2 is provided with a frame 20 which is connected to the front surface lower portion of the casing 1, three sets of circulatingly drivable belts 21*a* to 21*c* which are positioned on an upper surface portion 20*a* of the frame 20, and two pushers 22*a*, 22*b* (see FIG. 2) which are movable in the horizontal direction. In the transport apparatus 2, when the rack 3 is introduced into the position indicated by the symbol n1, then the rack 3 is transported in the direction of the arrow N1 by the belts 21*a*, and then the rack 3 is transported in the direction of the arrow N2 by the pusher 22*a* on the transport route 29. The rack 3 is intermittently fed at the arrangement pitch of the plurality of blood collecting tubes 30 on the transport route 29. When the rack 3 arrives at the terminal end of the transport route 29, then the rack 3 is transported in the direction of the arrow N3 by the belts 21*c*, and then the rack 3 is transported in the direction of the arrow N4 by the pusher 22*b* so that the rack 3 is supplied onto the belts 21*b*. The area, in which the belts 21*b* are provided, is the stock area for the racks 3 which accommodate the blood samples B completed for the analysis process. The rack 3, which is supplied to the stock area, is transported in the direction of the arrow N5 by the belts 21*b*. However, the rack 3 disposed on the belts 21*b* is prevented from the collision with the rack 3 transported in the direction of the arrow N2 owing to the presence of a stopper 23. The stock area effectively utilizes the space provided between the belts 21*a* and the belts 21*c*.

Figure 4:
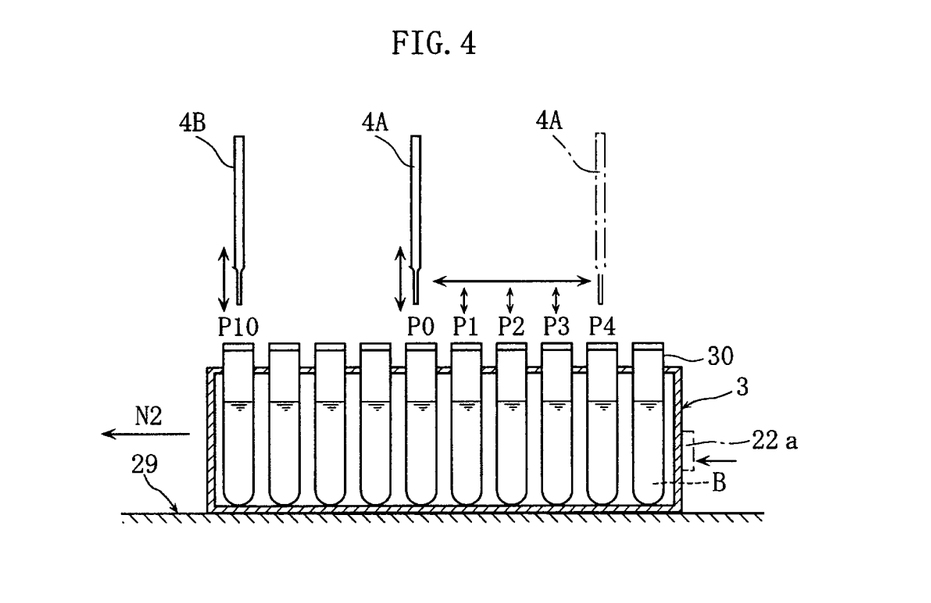
FIG. 4 illustrates an operation mode of first and second nozzles of the analysis apparatus shown in FIG. 1.

The first and second nozzles 4A, 4B collect the blood B from the blood collecting tube 30 on the transport route 29. As shown in FIG. 4, the sample collecting position of the second nozzle 4B is, for example, the position P10, which is invariable. On the contrary, the sample collecting position of the first nozzle 4A is changeable in the rack transport direction N2 and the direction opposite thereto, which can be changed to any one of the positions P0 to P4. The changing operation for changing the sample collecting position of the first nozzle 4A is controlled by the control unit 61, which is executed when the predetermined waiting state is provided such that the driving of the transport apparatus 2 is stopped, resulting from the interruption or the stop of the analysis process of the second analysis unit A2. However, details thereof will be described later on.

Figure 5:
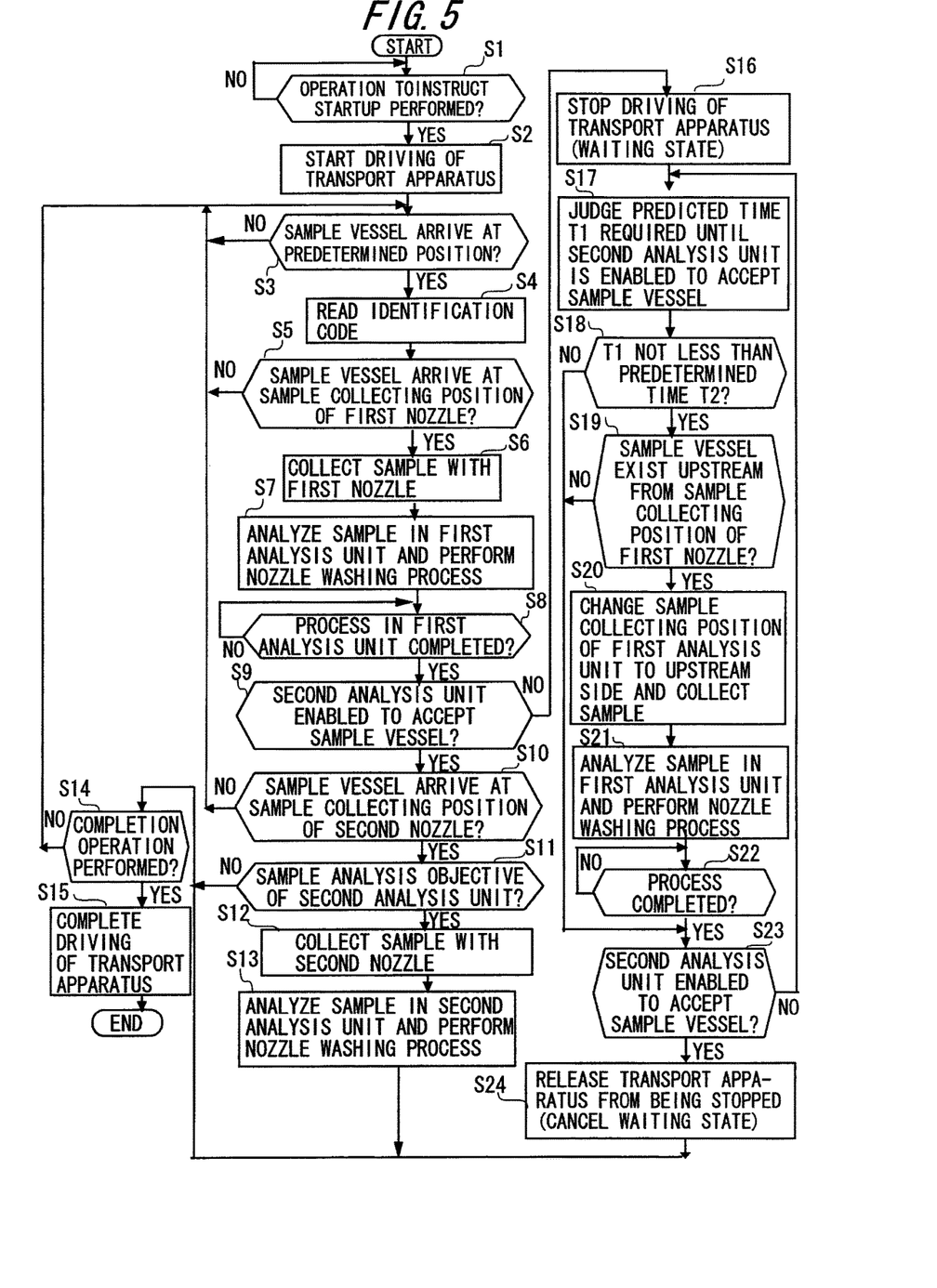
FIG. 5 shows a flow chart illustrating an exemplary operation process procedure of a control unit included in the analysis apparatus shown in FIG. 1.

Next, an explanation will be made with reference to a flow chart shown in FIG. 5 about an example of the analysis method based on the use of the analysis apparatus S and an example of the operation process procedure of the control unit 61.

At first, when the switch operation is performed to instruct the startup of the analysis unit S (S1: YES), the control unit 61 starts the driving of the transport apparatus 2 (S2). Accordingly, the rack 3, which is introduced into the position indicated by the arrow n1, can be successively transported along the route indicated by the arrows N1 to N5 described above. As described above, the rack 3 is intermittently transported at the arrangement pitch of the blood collecting tube B on the transport route 29.

The identification code 31 of the blood collecting tube 30 is firstly read by the reading unit 62 during the process in which the rack 3 is transported on the transport route 29 (S3: YES, S4). Subsequently, when the blood collecting tube 30 arrives at the sample collecting position of the first nozzle 4A, then the blood B is collected by the first nozzle 4A, and then the blood B is analyzed (glucose concentration is measured) in the first analysis unit A1. After that, the washing process is performed for the first nozzle 4A (S6, S7). When the process as described above is completed (S8: YES), the control unit 61 judges whether or not the second analysis unit A2 is in such a condition that the blood collecting tube 30 can be accepted (condition under which any malfunction or inconvenience does not arise even when the rack 3 is transported from the side of the first analysis unit A1 toward the second analysis unit A2) (S9): If the blood collecting tube 30 can be accepted (S9: YES), then the driving stop of the transport apparatus 2 (setting of the waiting state) is not performed unlike the case described later on, and the intermittent transport of the rack 3 is continuously executed on the transport route 29. In this case, the intermittent transport of the rack 3 is performed by repeating such an operation that the transport of the rack 3 is temporarily stopped from the point in time at which the blood collecting tube 30 arrives at the sample collecting position of the first nozzle 4A to the point in time at which the process in the first analysis unit A1 is completed as described above, and the transport of the rack 3 is temporarily stopped again at the point in time at which the rack 3 is transported by the predetermined pitch after the transport of the rack 3 is started thereafter.

When the blood collecting tube 30 arrives at the sample collecting position P10 of the second nozzle 4B (S10), the control unit 61 judges whether or not the blood B, which is accommodated in the blood collecting tube 30, is the analysis objective of the second analysis unit A2 (S11). The blood sample B, in which the measured value of the glucose concentration is within a predetermined normal range, is not the analysis objective of the second analysis unit A2. It is necessary to perform the more accurate or precise analysis for the blood samples B other than the above. Therefore, the blood samples B other than the above are the analysis objectives of the second analysis unit A2. If it is judged that the blood sample B is the analysis objective, then the blood B is collected by the second nozzle 4B, the blood B is analyzed (glycohemoglobin concentration is measured), and the washing process is performed for the second nozzle 4B (S11: YES, S12, S13). If the switch operation is performed to complete the analysis process, then the driving of the transport apparatus 2 is stopped (S14: YES, S15), and the analysis process is completed. However, if the switch operation is not performed, the series of operations as described above are basically repeated (S14: NO, S3).

In Step S9, the second analysis unit A2 is not in such a condition that the blood collecting tube 30 can be accepted (S9: NO) in some cases. For example, the case in which the process is interrupted in the second analysis unit A2 and the analysis process for the blood B is in execution in the second analysis unit A2 and the case in which the second nozzle 4B is in washing fall under the case as described above. Further, the case in which the operation is temporarily stopped, for example, due to the execution of any maintenance applied to the second analysis unit A2 also falls under the case as described above. In such situations, the control unit 61 provides the waiting state in which the driving of the transport apparatus 2 is stopped (S16).

Subsequently, the control unit 61 predicts the time T1 required until the second analysis unit A2 can accept the blood collecting tube 30 on the basis of, for example, the progress situation of the analysis process in the second analysis unit A2 (S17). If the predicted time T1 is not less than a predetermined time T2, and the next blood collecting tube 30 exists on the upstream side in the rack transport direction N2 from the sample collecting position of the first nozzle 4A, then the sample collecting position of the first nozzle 4A is changed, the blood B is collected from the blood collecting tube 30, and the analysis process therefor is performed (S18: YES, S19: YES, S20, S21). According to the process as described above, when the sample collecting position of the first nozzle 4A is the position P0, then the sample collecting position is changed to the position P1, and the blood B existing at the position P1 is collected so that the analysis process therefor is executed (see FIG. 4 as well).

The predetermined time T2 described above is, for example, 18 seconds, which is the same as the period of time required to analyze one sample in the first analysis unit A1. If the period of time, which elapses until the second analysis unit A2 can accept the blood collecting tube 30, is longer than the period of time required for the analysis, the blood B, which is collected at the position P1, can be appropriately analyzed in the first analysis unit A1 so that the analysis process is not delayed in the second analysis unit A2. If the predicted time T1 is less than the predetermined time T2 (S18: NO), or if the blood collecting tube 30 is absent at the position P1 (S19: NO), then the analysis process, which accompanies the change of the sample collecting position of the first nozzle 4A as described above, is not performed. However, in the present invention, the following procedure can be also constructed. That is, the control of Steps S17, S18 is omitted. If the waiting state, in which the driving of the transport apparatus 2 is stopped, is set, the sample collecting position of the first nozzle 4A is immediately changed.

If the analysis of the blood B collected from the blood collecting tube 30 at the position P1 and the washing process for the first nozzle 4A are completed, the control unit 61 judges again whether or not the second analysis unit A2 is in such a condition that the blood collecting tube 30 can be accepted (S22: YES, S23). If the second analysis unit A2 is not in such a condition yet that the blood collecting tube 30 can be accepted, due to the interruption or the stop of the process in the second analysis unit A2 (S23: NO), the control of Steps S17 to S22 described above is executed again. The analysis process speed of the second analysis unit A2 is slower than that of the first analysis unit A1. Therefore, the interruption of the process tends to arise in the second analysis unit A2. If the predicted time T1 is not less than the predetermined time T2, and the next blood collecting tube 30 exists on the upstream side in the rack transport direction N2 from the sample collecting position of the first nozzle 4A, then the collection of the blood B accompanied with the change of the sample collecting position of the first nozzle 4A and the analysis process therefor are repeated a plurality of times. According to the series of the operation control as described above, the sample collecting position of the first nozzle 4A can be successively changed to the positions P1 to P4 shown in FIG. 4, and the analysis process can be performed for a plurality of the blood samples B. When the second analysis unit A2 is in such a condition that the blood collecting tube 30 can be accepted, the transport apparatus 2 is released from the driving stop state (S23: YES, S24). After that, the series of the control operations in Step S3 and the followings are repeated unless the completion operation is performed (S14: NO). Although omitted from the flow chart shown in FIG. 5, the timing, at which the sample collecting position of the first nozzle 4A is restored to the original position P0, is provided, for example, after the completion of the collection of the blood B at the position P4 disposed on the most upstream side and the process therefor. However, there is no limitation thereto.

According to the analysis method described above, even when the situation (waiting state), in which it is difficult to transport the blood collecting tube 30, is provided due to the interruption or the stop of the process in the second analysis unit A2, then the first analysis unit A1 can be operated efficiently, and it is possible to shorten the period of time in which both of the first and second analysis units A1, A2 stop the operations thereof. Accordingly, it is possible to enhance the analysis process efficiency of the entire analysis apparatus S. Further, it is unnecessary that any area to stock a large number of racks 3 should be formed with a large size between the first and second analysis units A1, A2 as the means for increasing the operating ratio of the first analysis unit A1. Therefore, it is possible to suppress the transport apparatus 2 from being large-sized as well.

Figure 6:
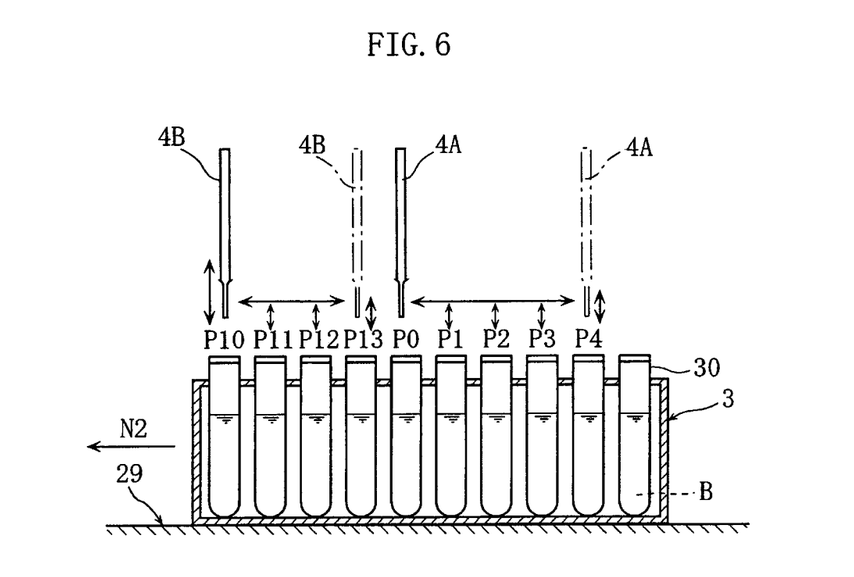
FIG. 6 illustrates another operation mode of the first and second nozzles in relation to the analysis apparatus according to the present invention.

In the analysis apparatus S described above, the sample collecting position can be changed in the rack transport direction N2 and the direction opposite thereto in relation to the second nozzle 4B as well in addition to the first nozzle 4A. Specifically, as shown in FIG. 6, the sample collecting position of the second nozzle 4B can be changed, for example, to the positions P10 to P13. The positions P10 to P13 are disposed in the downstream region in the rack transport direction N2 as compared with the first nozzle 4A.

Figure 7:
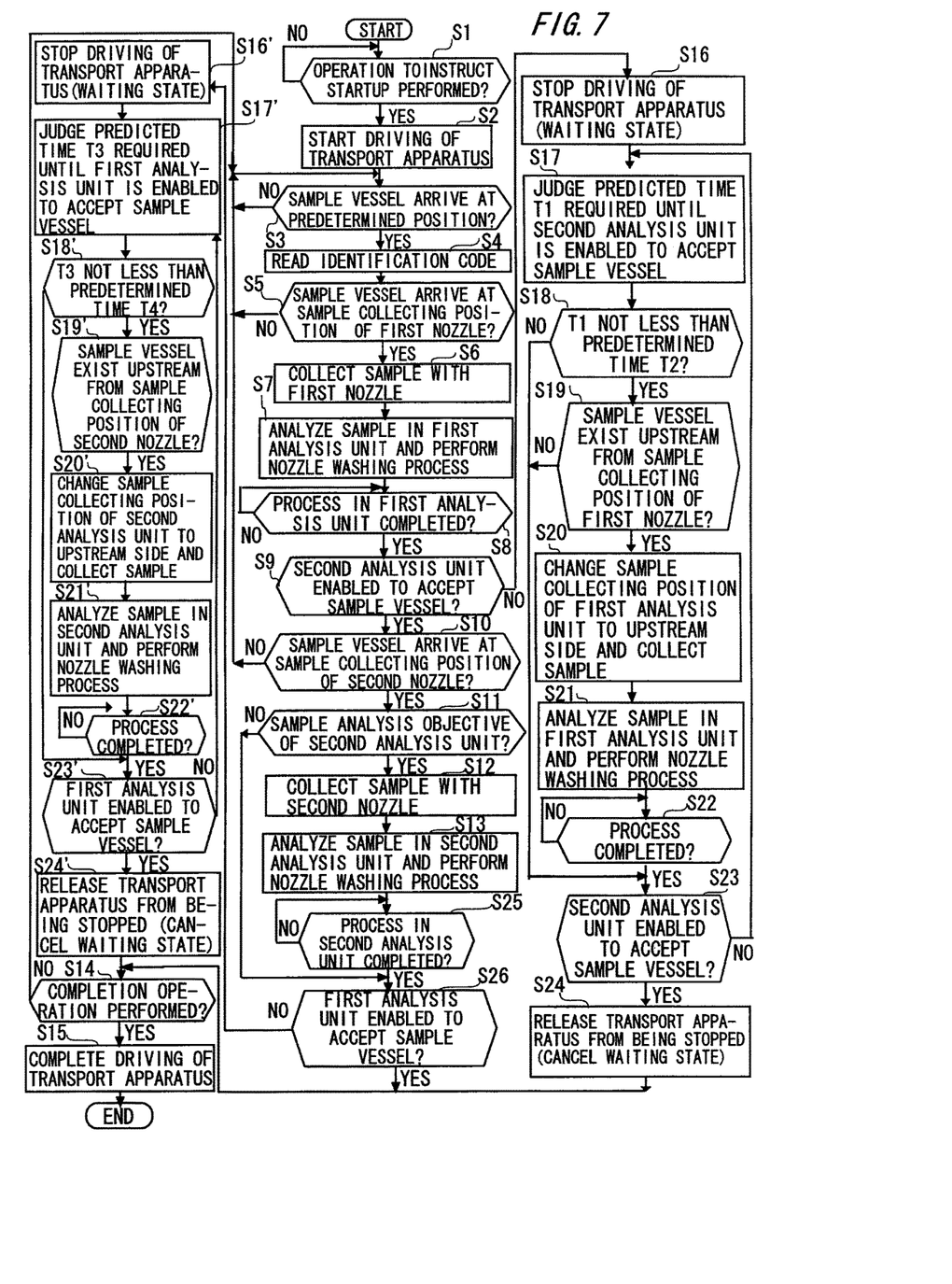
FIG. 7 shows a flow chart illustrating an exemplary operation process procedure of the control unit to provide the operation mode of the first and second nozzles shown in FIG. 6.

A flow chart shown in FIG. 7 shows an example of the operation process procedure of the control unit 61 applied when both of the sample collecting positions of the first and second nozzles 4A, 4B described above are made changeable. Steps S1 to S24 of the flow chart shown in FIG. 7 are the same as Steps S1 to S24 of the flow chart shown in FIG. 5. Therefore, even when the predetermined waiting state is provided resulting from the interruption or the stop of the second analysis unit A2, it is possible to continuously execute the analysis process for the blood B by the first analysis unit A1. The operation process shown in FIG. 7 is different from the operation process shown in FIG. 5 in that Steps S25, S26, S16' to S24' are further executed. This feature will be explained.

That is, when the process in the second analysis unit A2 shown in Step S13 is completed (S25), the control unit 61 judges whether or not the first analysis unit A1 is in such a condition that the blood collecting tube 30 can be accepted (S26). For example, if the interruption or the stop of the process is caused in the first analysis unit A1 for such a reason that the first nozzle 4A is washed for a long period of time, the first analysis unit A1 is not in the condition in which the blood collecting tube 30 can be accepted. In such a situation, the control unit 61 executes the processes of Steps S16' to S24'.

Steps S16' to S24' have the contents corresponding to those of Steps S16 to S24 described above. In the contents, the operation control, which is the same as or equivalent to the operation control for the first analysis unit A1 having been executed in Steps S16 to S24, is executed in the second analysis unit A2. More specifically, the control unit 61 provides the waiting state in which the driving of the transport apparatus 2 is stopped if the first analysis unit A1 is not in the condition in which the blood collecting tube 30 can be accepted (S26: YES, S16'). Subsequently, the control unit 61 predicts the time T3 required until the first analysis unit A1 is in the condition in which the blood collecting tube 30 can be accepted in consideration of, for example, the analysis process situation of the first analysis unit A1 (S17'). If the time T3 is not less than a predetermined time T4 (S18'), and the blood collecting tube 30 exists upstream in the rack transport direction N2 from the second nozzle 4B (S19'), then the sample collecting position of the second nozzle 4B is changed, the blood B is collected, and the analysis therefor is performed (S20', S21'). The predetermined time T4 is, for example, 36 seconds, which is the period of time required to analyze one sample in the second analysis unit A2. If the interruption or the stop of the process is prolonged in the first analysis unit A1, the sample collecting position of the second nozzle 4B is successively changed a plurality of times (S23': NO, S17'). Therefore, as shown in FIG. 6, the sample collecting position of the second analysis nozzle 4B may be successively changed from P10 to P11 and to P12, P13, and it is possible to execute the analysis process for the plurality of blood samples B. When the interruption or the stop of the process in the first analysis unit A1 disappears, and the first analysis unit A1 is in the condition in which the blood collecting tube 30 can be accepted, then the transport apparatus 2 is released from the driving stop state (waiting state), and it is possible to appropriately operate both of the first and second analysis units A1, A2 (S23': YES, S24').

According to the analysis method described above, it is possible to efficiently operate the second analysis unit A2 even in the case of such a situation that it is difficult to transport the blood collecting tube 30 on account of the interruption or the stop of the process in the first analysis unit A1. On the other hand, in the case of such a situation that it is difficult to transport the blood collecting tube 30 on account of the interruption or the stop of the process in the second analysis unit A2, it is possible to appropriately operate the first analysis unit A1 in the same manner as in the analysis method explained with reference to FIG. 5. Therefore, the analysis method is more preferred in order to enhance the analysis process efficiency of the entire analysis apparatus S.

Figure 8:
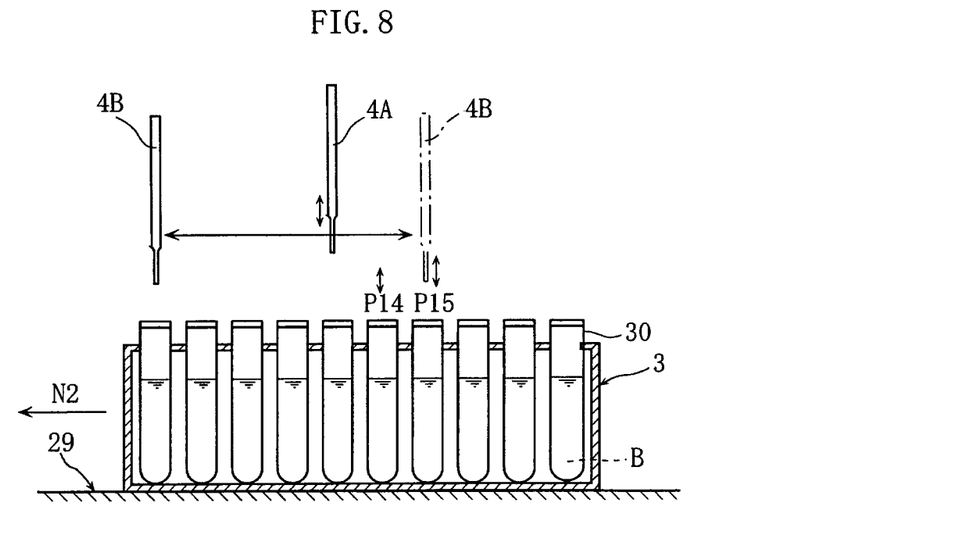
FIG. 8 illustrates still another operation mode of the first and second nozzles in relation to the analysis apparatus according to the present invention.
Figure 9:
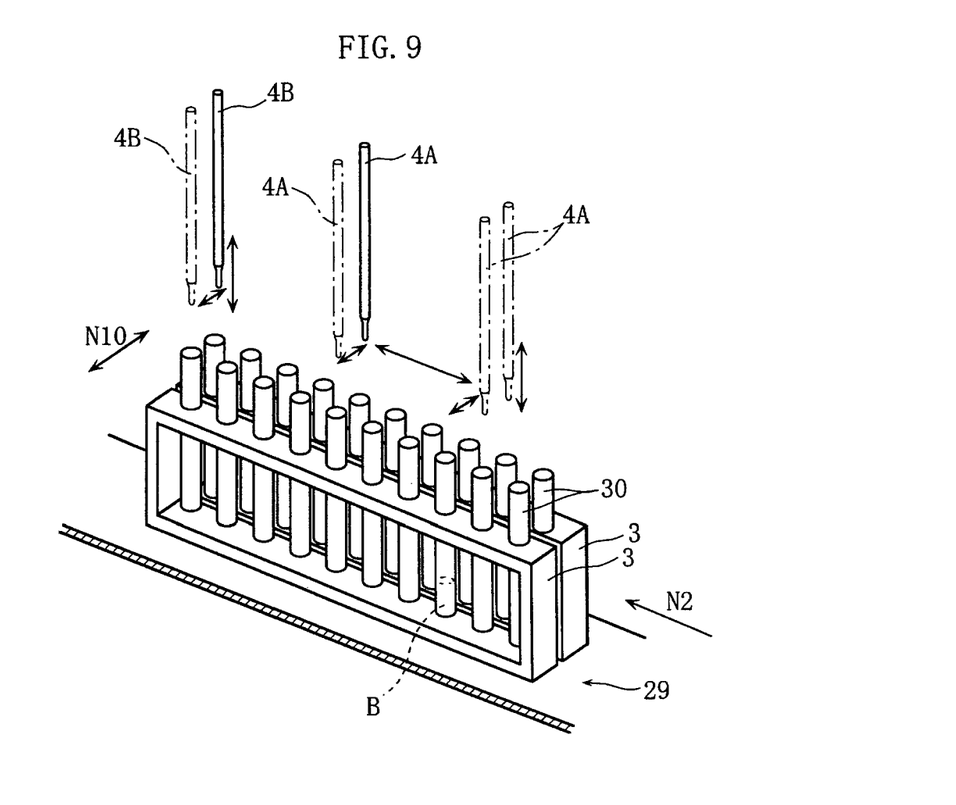
FIG. 9 illustrates still another operation mode of the first and second nozzles in relation to the analysis apparatus according to the present invention.
Figure 10:
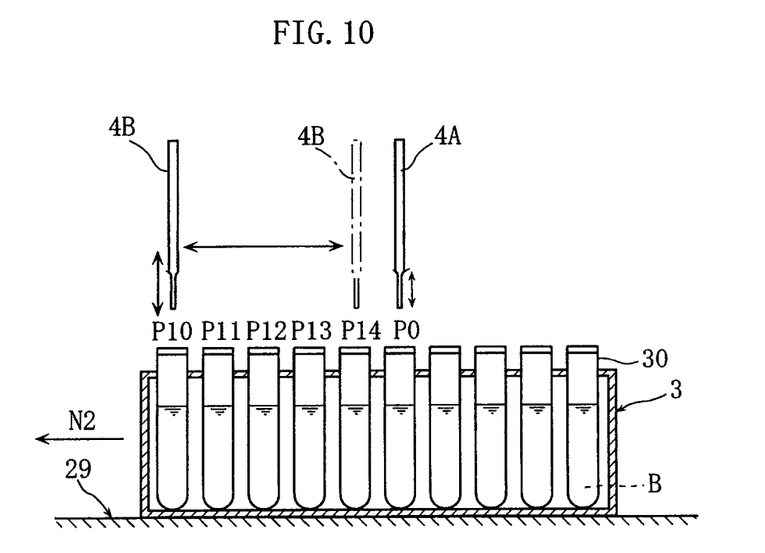
FIG. 10 illustrates still another operation mode of the first and second nozzles in relation to the analysis apparatus according to the present invention.

FIGS. 8 to 10 show other examples of the operation mode of the first and second nozzles 4A, 4B in the analysis apparatus S described above.

In an embodiment shown in FIG. 8, the sample collecting position of the second nozzle 4B can be also changed to the positions P14, P15 disposed upstream in the rack transport direction N2 from the first nozzle 4A. In this arrangement, when the second nozzle 4B is moved to the upstream area as compared with the first nozzle 4A, and when the second nozzle 4B is returned from the upstream area to the downstream area, then the first and second nozzles 4A, 4B do not interfere with each other.

In this embodiment, for example, when the process in the first analysis unit A1 is stopped for a relatively long period of time, it is possible to collect the blood samples B from a larger number of the blood collecting tubes 30 by utilizing the second nozzle 4B. Therefore, this embodiment is more preferred to enhance the analysis process efficiency of the entire analysis apparatus S. The blood B, which is contained in the blood collecting tube 30 existing in the upstream area from the first nozzle 4A, is not subjected to the analysis process yet by the first analysis unit A1. However, even when the blood B as described above is analyzed by the second analysis unit A2 prior to the first analysis unit A1, any inconvenience is not caused.

In an embodiment shown in FIG. 9, a plurality of racks 3 are aligned in two arrays and transported on the transport route 29. In relation thereto, the first nozzle 4A can change the sample collecting position in the direction N10 intersecting the rack transport direction N2 and the direction opposite thereto as well, in addition to the rack transport direction N2 and the direction opposite thereto. The sample collecting position of the second nozzle 4B can be also changed in the direction N10.

In this embodiment, the plurality of racks 3 can be transported efficiently while being aligned in two arrays. Further, it is possible to appropriately collect the blood sample B from any one of the blood collecting tubes 30 on the racks 3 in two arrays. When the blood B is collected from each of the blood collecting tubes 30 of the two racks 3 aligned in two arrays when the transport apparatus 2 is in the waiting state, the blood collection from the plurality of blood collecting tubes 30 on the other rack 3 is started after the operation, in which the blood samples B are collected from all of the plurality of blood collecting tubes 30 disposed on one rack 3, is completed. By doing so, it is possible to early execute the operation for delivering the one rack 3 to the second analysis unit A2, which is preferred in order to enhance the process efficiency. For example, a mode, in which the blood collecting tubes 30 are aligned in a plurality of arrays and held by one rack, may be also adopted as an example of the transport of the blood collecting tubes 30 in a plurality of arrays, in place of the transport of the racks 3 in a plurality of arrays.

In an embodiment shown in FIG. 10, the sample collecting position of the first nozzle 4A is invariable, which remains at the position P0. On the contrary, the second nozzle 4B is movable in the transport direction N2 of the rack 3 and the direction opposite thereto. The sample collecting position of the second nozzle 4B can be changed, for example, to the positions P10 to P14.

In this embodiment, when the process in the second analysis unit A2 is interrupted or stopped, and the transport apparatus 2 is in the waiting state, then it is impossible to change the sample collecting position of the first nozzle 4A. However, when the process in the first analysis unit A1 is interrupted or stopped, and the waiting state is provided, then the sample collecting position of the second nozzle 4B can be changed to operate the second analysis unit A2. Therefore, it is also possible to enhance the efficiency of the analysis process. The arrangement of this embodiment is preferably adopted when the analysis process in the first analysis unit A1 tends to be interrupted or stopped. As appreciated from this embodiment and the embodiments described above, the present invention includes the mode in which the sample collecting position of the second nozzle is changed while fixing the sample collecting position of the first nozzle, in addition to the mode in which the sample collecting position of the first nozzle is changed while fixing the sample collecting position of the second nozzle and the mode in which the sample collecting positions of both of the first and second nozzles are changed. It is allowable that the present invention is constructed in any mode.

The present invention is not limited to the contents of the embodiments described above.

It is appropriate that the first and second nozzles referred to in the present invention have the function to collect the sample from the sample vessel. The first and second nozzles may be in a form of simple tube made of, for example, rubber or resin. Any function or any mechanism, which is distinct from the sample collecting function, may be provided and appended to the first and second nozzles. For example, it is also possible to provide such an arrangement that a stirring mechanism for stirring the sample in the sample vessel, a washing mechanism for washing the sample vessel, and/or a mechanism for introducing a reagent into the sample vessel is/are provided and appended to the nozzle.

In the present invention, when the sample is collected while changing at least one of the sample collecting positions of the first and second nozzles, the sample, which is not subjected to the analysis process yet, is basically collected. However, there is no limitation thereto. For example, in the first and second analysis units, the analysis process of the same contents for one sample is repeated a plurality of times in some cases. In such a situation, when the sample is collected while changing the sample collecting position of the nozzle, the sample collection for the second time is performed from the sample vessel for which the sample collection for the first time has been already completed. The case, in which the operation is performed as described above, is also subsumed into the technical scope of the present invention.

The present invention is also applicable to an analysis apparatus in which three or more analysis units are connected. This case is subsumed into the technical scope of the present invention, provided that any two mutually adjacent analysis units of the three or more analysis units correspond to the first and second analysis units referred to in the present invention. In the analysis apparatus according to the present invention, it is also possible to adopt such an arrangement that the first and second analysis units are distinctly accommodated in two casings and the first and second analysis units are separated from each other. It is unnecessary to provide the stock area for stocking the sample vessels between the first and second analysis units. However, it is possible to adopt such an arrangement that the stock area as described above is intentionally provided. According to the present invention, an effect is obtained such that the stock area as described above can be small-sized.

The first and second analysis units referred to in the present invention are not limited to those which measure the concentration of the specified component of blood. For example, it is also possible to measure the concentration of a specified component of urine which is transported while being accommodated in a urine collecting tube. A specified example is referred to when urine is the examination objective. That is, it is possible to provide such an arrangement that the first analysis unit is an apparatus for urine qualitative analysis and the second analysis unit is an apparatus for urine sediment analysis. In the apparatus for urine qualitative analysis, for example, the measurement is executed for one or more items of urinary protein, urinary sugar, occult blood, and urobilinogen. In the apparatus for urine sediment analysis, for example, the detection and the measurement are executed for the hemocyte system, the epithelial cell system, the cylindrical system, the microbial system, the precipitate of crystal or salt system, or any other precipitate contained in urine. In the apparatus for urine qualitative analysis, the time required to analyze one sample is, for example, about 18 seconds, wherein substantially all of the supplied samples are the examination objectives. On the other hand, in the apparatus for urine sediment analysis, the time required to analyze one sample is, for example, about 36 to 39 seconds, wherein it is judged whether or not the measurement process is performed on the basis of the measurement result obtained by the apparatus for urine qualitative analysis, and about 50% of the supplied samples are the examination objectives. However, in the present invention, any substance other than blood and urine can be used as the sample. It is also possible to provide such an arrangement that the sample vessels are transported without using the rack.

The invention claimed is:

1. An analysis method of an analysis apparatus, the method comprising:
   transporting a rack holding a plurality of sample vessels on a predetermined transport route, wherein the analysis apparatus includes a first analysis unit having a first nozzle and a second analysis unit having a second nozzle, and the predetermined transport route includes a route to transport the rack holding the plurality of sample vessels from the first analysis unit to the second analysis unit;
   the analysis method further comprising a controller controlling operations of the first analysis unit, the second analysis unit, and the transporting of the rack holding the plurality of the sample vessels along the predetermined transport route;
   the controller configured to control:
   collecting samples from the plurality of sample vessels held by the rack on the predetermined transport route using the first nozzle which is in a first position over the predetermined transport route;
   executing, by the first analysis unit, a first analysis process for the samples collected by the first nozzle;
   collecting samples from the plurality of sample vessels held by the rack, which is transported through the predetermined transport route, using the second nozzle which is in a second position over the predetermined transport route, the second position being different from the first position;

executing, by the second analysis unit, a second analysis process for the samples collected by the second nozzle; and a position of the first nozzle over the predetermined transport route when transport of the rack holding the plurality of sample vessels on the predetermined transport route is interrupted or stopped so that the first nozzle collects samples at a position over the predetermined transport route other than the first position from a sample vessel on the predetermined transport route or a position of the second nozzle over the predetermined transport route when transport of the rack holding the plurality of sample vessels on the predetermined transport route is interrupted or stopped so that the second nozzle collects samples at a position over the predetermined transport route other than the second position from a sample vessel on the predetermined transport route.

2. An analysis method according to claim 1, wherein
the position of the second nozzle is changed to collect the samples from the plurality of sample vessels so that the analysis process for the sample is executed by the second analysis unit when the transport of the rack holding the plurality of sample vessels on the predetermined transport route is interrupted or stopped based on the interruption or the stop of the analysis process in the first analysis unit; and while the position of the first nozzle is changed to collect the samples from the plurality of sample vessels so that the analysis process for the sample is executed by the first analysis unit when the transport of the rack holding the plurality of sample vessels on the predetermined transport route is interrupted or stopped based on the interruption or the stop of the analysis process in the second analysis unit.

3. An analysis apparatus comprising:

a transport apparatus which transports a rack holding a plurality of sample vessels on a predetermined transport route comprising:

a first analysis unit having a first nozzle;

a second analysis unit having a second nozzle; and a predetermined transport route including a route to transport the rack holding the plurality of sample vessels from the first analysis unit to the second analysis unit; and a controller for controlling the operations of the first analysis unit, a second analysis unit, and the transporting of the rack holding the plurality of the sample vessels along the predetermined transport route;

the controller configured to control:

collecting samples from the plurality of sample vessels held by the rack on the predetermined transport route using the first nozzle in a first position over the predetermined transport route and executing, by the first analysis unit, a first analysis process for the samples collected by the first nozzle;

collecting samples from the plurality of sample vessels held by the rack on the predetermined transport route using the second nozzle in a second position over the predetermined transport route, the second position being different from the first position, and executing, by the second analysis unit, a second analysis process for the sample collected by the second nozzle; and     a position of the first nozzle over the predetermined transport route when transport of the rack holding the plurality of sample vessels on the predetermined transport route is interrupted or stopped so that the first nozzle collects samples at a position over the predetermined transport route other than the first position from a sample vessel on the predetermined transport route or a position of the second nozzle over the predetermined transport route when transport of the rack holding the plurality of sample vessels on the predetermined transport route is interrupted or stopped so that the second nozzle collects samples at a position over the predetermined transport route other than the second position from a sample vessel on the predetermined transport route.

4. The analysis apparatus according to claim 3, wherein the controller is further configured to control:

the changing of position of the second nozzle to collect the samples from the plurality of sample vessels so that the analysis process for the sample is executed by the second analysis unit when the transport of the rack holding the plurality of sample vessels on the predetermined transport route is interrupted or stopped based on the interruption or the stop of the analysis process in the first analysis unit; and     while the position of the first nozzle is changed to collect the samples from the plurality of sample vessels so that the analysis process for the sample is executed by the first analysis unit when the transport of the rack holding the plurality of sample vessels on the predetermined transport route is interrupted or stopped based on the interruption or the stop of the analysis process in the second analysis unit.

5. The analysis apparatus according to claim 4, wherein the first nozzle is constructed so that the first position is changeable in a sample vessel transport direction and a direction opposite thereto, and the first position of the first nozzle is progressively changed in a direction opposite to the direction that the rack holding the plurality of samples is transported from the first analysis unit to the second analysis unit through the predetermined transport route.

6. The analysis apparatus according to claim 4, wherein the second nozzle is constructed so that the second position is changeable in a sample vessel transport direction and a direction opposite thereto, and the second position of the second nozzle is progressively changed in a direction opposite to the direction that the rack holding the plurality of samples is transported from the first analysis unit to the second analysis unit through the predetermined transport route.

7. The analysis apparatus according to claim 4, wherein the second nozzle is constructed so that the second position is changed until arrival at an upstream area in a sample vessel transport direction as compared with the first position of the first nozzle, and the second nozzle is capable of collecting the sample which is not collected by the first nozzle.

8. The analysis apparatus according to claim 4, wherein the first and second analysis units are accommodated and integrated in one casing.

9. The analysis apparatus according to claim 4, wherein:

at least one of the first and second analysis units is constructed to analyze only a part of the selected sample or samples of the plurality of supplied samples; and a number of the sample or samples subjected to the analysis differs between the first and second analysis units.

10. The analysis apparatus according to claim 4, wherein the first and second analysis units require different amounts of time to analyze one sample.

11. The analysis apparatus according to claim 9, wherein the first analysis unit deals with a large number of the samples subjected to the analysis as compared with the second analysis unit, and the first analysis unit is constructed to require a short period of time required to analyze one sample as compared with the second analysis unit.

12. A collecting apparatus comprising:
a transport unit which transports a rack holding a plurality of sample vessels along a predetermined transport route;
a first nozzle which collects samples from the plurality of sample vessels held by the rack transported by the transport unit to supply the samples to a predetermined portion;
a second nozzle which collects samples from the plurality of sample vessels held by the rack on a downstream side in the predetermined transport route from the first nozzle to supply the samples to a predetermined portion; and
a controller configured to control the first and second nozzles, the controller changing a sample collecting position of the second nozzle from an initial sample collecting position over the predetermined transport route to an alternate sample collecting position over the predetermined transport route to collect samples from the plurality of sample vessels when a predetermined waiting state is provided such that the transport of the rack holding the plurality of sample vessels is interrupted or stopped or changing a sample collecting position of the first nozzle from an initial sample collecting position over the predetermined transport route to an alternate sample collecting position over the predetermined transport route to collect samples from the plurality of sample vessels when the predetermined waiting state is provided such that the transport of the rack holding the plurality of sample vessels is interrupted or stopped,
wherein the predetermined transport route includes a route to transport the rack holding the plurality of sample vessels from the first nozzle to the second nozzle.

13. An analysis method according to claim 1, wherein the controlling of a position of the first nozzle is started when transport of the rack holding the plurality of sample vessels on the predetermined route is interrupted or stopped by interruption or stop of the second analysis process.

14. An analysis method according to claim 1, wherein the controlling of a position of the second nozzle is started when transport of the rack holding the plurality of sample vessels on the predetermined route is interrupted or stopped by interruption or stop of the first analysis process.

* * * * *